(12) United States Patent
Rosen et al.

(10) Patent No.: US 11,956,276 B2
(45) Date of Patent: Apr. 9, 2024

(54) SYSTEMS AND METHODS FOR SWITCHING BETWEEN COMMUNICATION CHANNELS USING SECURE HEALTHCARE COMMUNICATION SYSTEM

(71) Applicant: LifeWIRE Corporation, Toronto (CA)

(72) Inventors: Howard Rosen, Toronto (CA); Donald Whitbeck, Toronto (CA); Chaitanya Marvici, Toronto (CA)

(73) Assignee: LifeWIRE Corporation, Toronto (CA)

(*) Notice: Subject to any disclaimer, the term of this patent is extended or adjusted under 35 U.S.C. 154(b) by 20 days.

(21) Appl. No.: 17/934,971

(22) Filed: Sep. 23, 2022

(65) Prior Publication Data

US 2023/0053697 A1    Feb. 23, 2023

Related U.S. Application Data (63) Continuation of application No. 16/836,220, filed on Mar. 31, 2020, now Pat. No. 11,489,871.

(51) Int. Cl.
| | |
|---|---|
| *H04L 29/06* | (2006.01) |
| *G06K 7/14* | (2006.01) |
| *G16H 10/20* | (2018.01) |
| *G16H 80/00* | (2018.01) |
| *H04L 9/32* | (2006.01) |
| *H04L 9/40* | (2022.01) |

(52) U.S. Cl.
CPC .......... *H04L 63/18* (2013.01); *G06K 7/1413* (2013.01); *G06K 7/1417* (2013.01); *G16H 10/20* (2018.01); *G16H 80/00* (2018.01); *H04L 9/3215* (2013.01); *H04L 63/0428* (2013.01)

(58) Field of Classification Search
CPC ...................................................... H04L 63/18
See application file for complete search history.

(56) References Cited

U.S. PATENT DOCUMENTS

| | | | |
|---|---|---|---|
| 2015/0363557 A1* | 12/2015 | Van Arkel ............ | G06Q 40/08 705/2 |
| 2019/0349652 A1* | 11/2019 | Greenewald ......... | H04B 5/0025 |
| 2020/0019726 A1* | 1/2020 | Perecman ............. | G06F 21/40 |
| 2020/0350082 A1* | 11/2020 | Davison ................ | G16H 80/00 |

* cited by examiner

*Primary Examiner* — Bradley W Holder
(74) *Attorney, Agent, or Firm* — Finnegan, Henderson, Farabow, Garrett & Dunner LLP (57) ABSTRACT

A system for switching between communication platforms using a secure healthcare communication system the system comprising: a healthcare provider server device. Transmitting a communication switch request to a first communication platform and establish a first communication channel between the user device and the healthcare provider server device to communicate one or more messages to the first communication platform. Transmit an encoded message over the first communication channel to the first communication platform in response to receiving the communication switch initiation request, the encoded message including an identifier associated with a second communication platform. Switch to an encrypted second communication channel from the first communication channel in response to receiving an encrypted communication initiation request. Encrypted communication initiation request is generated based on the identifier.

19 Claims, 6 Drawing Sheets

SYSTEMS AND METHODS FOR SWITCHING BETWEEN COMMUNICATION CHANNELS USING SECURE HEALTHCARE COMMUNICATION SYSTEM

RELATED APPLICATIONS

This application is a continuation of U.S. application Ser. No. 16/836,220 (now U.S. Pat. No. 11,489,871), filed Mar. 31, 2020, which is incorporated herein by reference.

TECHNICAL FIELD

This disclosure relates generally to the field of a healthcare communication system. More specifically, and without limitation, embodiments of the present disclosure relate to systems and methods for switching between communication channels using secure healthcare communication system.

BACKGROUND

Care providers, such as healthcare providers, doctors, nurses, physicians, parents, social workers, or other similar providers of care, must often communicate frequently with those receiving theft care (i.e. care receivers such as patients, elderly persons, children, or other users that may receive care or assistance from a care provider). These care providers are often tasked with following up with their care receivers, checking on their status, receiving updates, and providing reminders and/or other messages related to the care receivers' care. Further, at times care receivers may need reminder messages from their care providers for various reasons, for example, to follow up with the care receivers an how they are reacting to a prescribed medicine, to schedule an annual checkup appointment, or to check a care receivers health, etc.

Care receivers can often share a communication device among family members or may use a communication device that is accessible by other users. For example, these may include individuals who receive Medicare, Medicaid, and/or are financially challenged and cannot afford communication devices for each individual. Sharing of communication device often results in communications between care receivers and care providers being accessible by other family members, users or other individuals. Unfortunately, this would result in the patient's privacy being compromised. As a result, care providers have to be careful about disclosing sensitive information and further have to be careful about violating Health Insurance Portability and Accountability Act (HIPAA) laws.

Further, many care receivers use various communication platforms such as, web browser, text messaging applications such as short messaging services (SMS) messaging, video calling applications, audio call applications or social networking applications such as Facebook messenger or Whatsapp, based on their circumstances or preferences. For example, many care receivers residing in rural areas have poor access to cell coverage because of which they prefer texting messaging over email or video communications, many care receivers do not have smart mobile phones or the ability to download separate mobile applications for communication, further some care receivers prefer to communicate via short messaging services (SMS) messaging, while others prefer to communicate via email or social networking applications like Facebook messenger.

Switching between different communication platforms is difficult to do because many times care receivers would lose access to previous communications on a different communication platform upon switching and many times as the previous communications may be deleted from the communication device resulting in no record of previous communications. By not having access to previous communications care providers and care receivers would not be able to review previous communications that may include vital information, such as a care receivers previous health conditions, medications prescribed to the care receiver, etc which may be utilized by care providers for future treatments. These issues need to be solved in order for care providers to effectively and securely communicate with care receivers and other users.

Further, care receivers communicate with their care providers (e.g. health care providers) via various communication platforms using various communication devices (e.g., mobile phone, personal computer, laptop, tablet, etc.) to receive their records (e.g., medical records), ask and/or respond to follow up questions. Some care receivers may prefer to keep their communications private communications may be required to be protected under local, state or federal regulations.

If a care receiver uses a communication device that is shared by his/her family members or uses a communication device that is accessible by other users, then their communications with the health care providers would be accessible by other family members or users. In some instances, the care provider may not be allowed to communicate with an individual other than the care receiver. This again results in the patient's privacy being compromised.

Further, each time a care receiver communicates with health care providers, the care receiver does not have access to his/her previous communications. By way of example, when the care receiver utilizes a first communication device to initiate communication with health care providers over a particular platform and then switches to a different communication device for future communications over a another communication platform, the care receiver cannot access previous communications. This results in an inefficient communication method that limits care receivers and care providers alike from accessing vital information seamlessly over multiple communication devices. This causes technical disadvantages of not being able to transition care receiver data over multiple communication platforms.

Accordingly, there is a need for a system that provides a technical solution for the above-noted problems.

SUMMARY

In accordance with embodiments of the present disclosure, there is provided a system for switching between communication platforms using a secure healthcare communication system, the system comprising: a healthcare provider server device comprising: one or more memory devices storing instructions; and one or n ore processors configured to execute the instructions to: transmit a communication switch request to a first communication platform on a user device associated with a care receiver based on preferences stored in a database. Establish a first communication channel between the user device and the healthcare provider server device to communicate one or more messages to the first communication platform. Communicate the one or more messages over the first communication channel to the first communication platform. Receive a communication switch initiation request from the user device. Transmit an encoded message over the first communication channel to the first communication platform in response to receiving the communication switch initiation request, the encoded message including an identifier associated with a second communication platform. Store the one or more messages communicated over the first communication channel as a first set of messages in the database. Switch to an encrypted second communication channel from the first communication channel in response to receiving an encrypted communication initiation request, wherein the encrypted communication initiation request is generated based on the identifier and wherein the encrypted second communication channel is established between the user device and the healthcare provider server device to communicate with the second communication platform. Retrieve the first set of messages stored in the database. Transmit the retrieved first set of messages for display on the second communication platform over the encrypted second communication channel.

In accordance with embodiments of the present disclosure, there is also provided a computer implemented method for switching between communication platforms using a secure healthcare communication system comprising a healthcare provider server device, the method comprising: transmitting a communication switch request to a first communication platform on a user device associated with a care receiver based on preferences stored in a database. Establishing a first communication channel between the user device and the healthcare provider server device to communicate one or more messages to the first communication platform.

Communicating the one or more messages over the first communication channel to the first communication platform. Receiving a communication switch initiation request from the user device. Transmitting an encoded message over the first communication channel to the first communication platform in response to receiving the communication switch initiation request, the encoded message including an identifier associated with a second communication platform. Storing the one or more messages communicated over the first communication channel as a first set of messages in the database. Switching to an encrypted second communication channel from the first communication channel in response to receiving an encrypted communication initiation request, wherein the encrypted communication initiation request is generated based on the identifier and wherein the encrypted second communication channel is established between the user device and the healthcare provider server device to communicate with the second communication platform. Retrieving the first set of messages stored in the database. Transmit the retrieved first set of messages for display on the second communication platform over the encrypted second communication channel.

In accordance with embodiments of the present disclosure, there is further provided a non-transitory computer-readable medium storing instructions executable by one or more processors to perform operations for switching between communication platforms using a secure healthcare communication system comprising a healthcare provider server device, the operations comprising: transmitting a communication switch request to a first communication platform on a user device associated with a care receiver based on preferences stored in a database. Establishing a first communication channel between the user device and the healthcare provider server device to communicate one or more messages to the first communication platform.

Communicating the one or more messages over the first communication channel to the first communication platform. Receiving a communication switch initiation request from the user device. Transmitting an encoded message over the first communication channel to the first communication platform in response to receiving the communication switch initiation request, the encoded message including an identifier associated with a second communication platform. Storing the one or more messages communicated over the first communication channel as a first set of messages in the database. Switching to an encrypted second communication channel from the first communication channel in response to receiving an encrypted communication initiation request, wherein the encrypted communication initiation request is generated based on the identifier and wherein the encrypted second communication channel is established between the user device and the healthcare provider server device to communicate with the second communication platform. Retrieving the first set of messages stored in the database. Transmit the retrieved first set of messages for display on the second communication platform over the encrypted second communication channel.

BRIEF DESCRIPTION OF DRAWINGS

The accompanying drawings, which are incorporated in and constitute a part of his specification, illustrate disclosed embodiments and, together with the description, serve to explain the disclosed embodiments. In the drawings.

DETAILED DESCRIPTION

Reference will now be made in detail to the disclosed embodiments, examples of which are illustrated in the accompanying drawings. Wherever convenient, the same reference numbers will be used throughout the drawings to refer to the same or like parts.

While the following description is directed to switching between communication channels using a secure healthcare communication system, it should be appreciated that the present disclosure is not limited to the specific disclosed embodiments and details, which are exemplary only. It is further understood that one possessing ordinary skill in the art, would appreciate the use of the embodiments of the present disclosure for their intended purposes and benefits in any number of alternative embodiments, depending on specific design and other needs.

Figure 1:
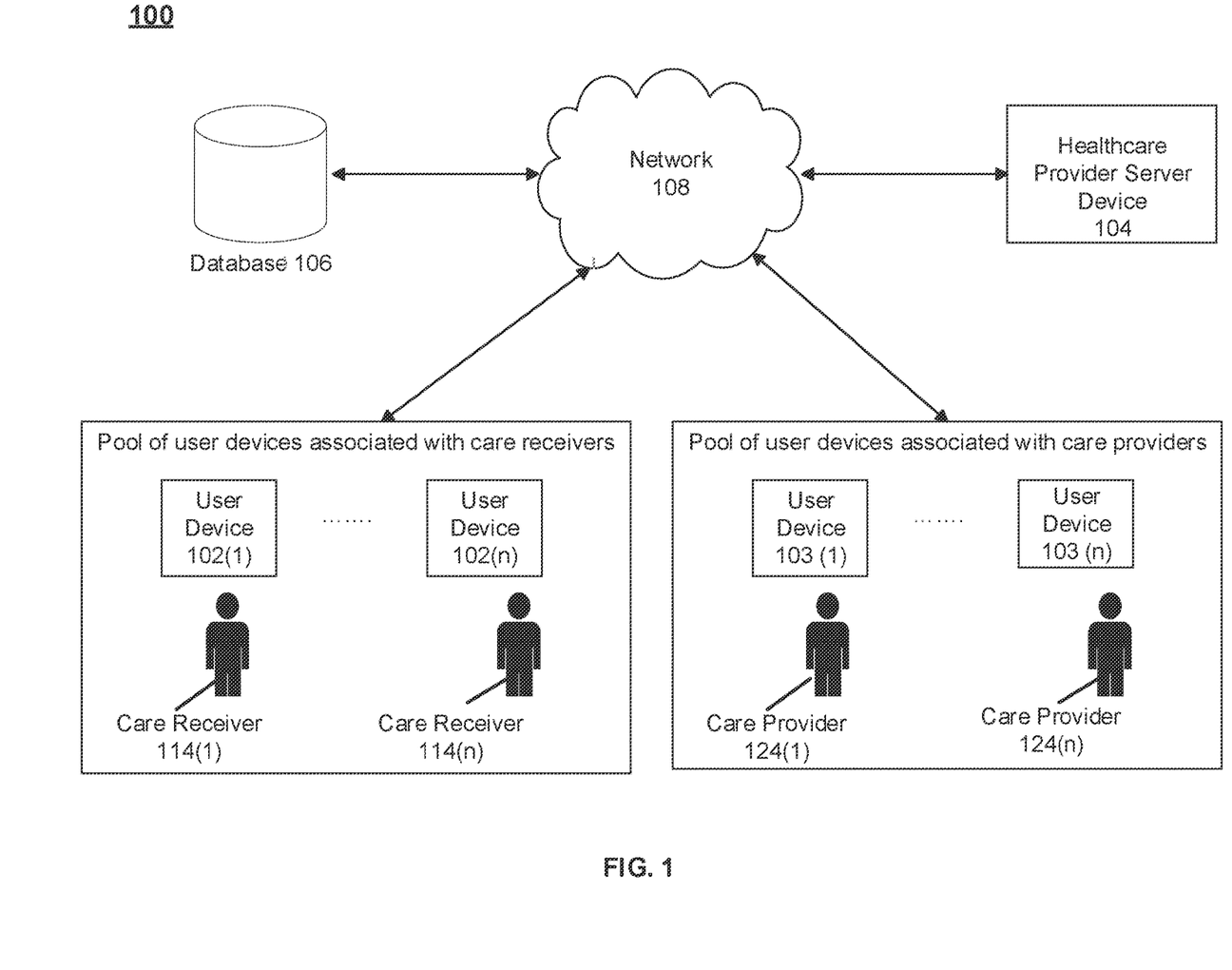
FIG. 1 is a block diagram of an exemplary system, consistent with disclosed embodiments.

FIG. 1 is a block diagram of an exemplary system 100, for performing one or more operations consistent with disclosed embodiments. In some embodiments, system 100 includes one or more user devices associated with care receivers 102(1), 102(2), . . . 102(n), one or more user devices associated with care providers 103(1), 103(2), . . . 103(n), one or more healthcare provider servers 104, one or more databases 106, and a network 108. The components and arrangement of the components included in system 100 may vary, Thus, system 100 may include other components that perform or assist in the performance of one or more operations consistent with the disclosed embodiments.

As more fully described below, user devices associated with care receivers 102(1)-102(n), user devices associated with care providers 103(1)-103(n) and healthcare provider server device 104 may include one or more computing devices (e.g., computer(s), server(s), etc.), memory storing data and/or software instructions (e.g., database(s), memory devices, etc.), and other known computing components. In some embodiments, the one or more computing devices may be configured to execute software instructions stored in the memory to perform one or more operations consistent with the disclosed embodiments. Aspects of healthcare provider server device(s) 104, database(s) 106, and user devices 102(1)-102(n) and 103(1)-103(n) may be configured to communicate with one or more other components of system 100 via network 108, for example. In certain aspects, care receivers 114(1)-114(n) are respectively associated with and operate user devices 102(1)-102(n), and care providers 124(1)-124(n) are respectively associated with and operate user devices 103(1)-103(n), to interact with one or more components of system 100 by sending and receiving communications, initiating operations, and/or providing input for one or more operations consistent with the disclosed embodiments. For example, care receivers 114(1)-114(n) may include patients, elderly persons, children, or other users that may receive care or assistance from a care provider. For example, care providers 124(1)-124(n) may include healthcare providers, doctors, nurses, physicians, parents, social workers, or other similar providers of care.

Care receivers may include patients, elderly persons, children, or other users that may receive care or assistance from a care provider. By way of example, care receiver 114(1) may be a patient who receives care from a care provider 124(1). Care providers may include healthcare providers, doctors, nurses, physicians, parents, social workers, or other similar providers of care. By way of example, care provider 124(1) may be a doctor who is currently treating the patient/care receiver 114(1). The care receiver 114(1) and the care provider 124(1) may have respective accounts registered with healthcare provider server device 104. The care receivers 114(1)-114(n) may register and access their account profiles stored at the database 106 via user devices 102(1)-102(n), for example using a mobile application stored on the user device or a web application/browser. By way of example, care receiver 114(1) may access their account profiles to create a trusted care providers list, that includes one or more of the care providers 124(1)-124(n) selected as being trusted by the care receiver 114(1). Here, the care receiver 114(1) may be a patient who has included, in his account profile, the care provider 124(1) who is the patient's doctor, as a trusted person who can communicate with the care receiver 114(1) over the healthcare provider server device 104, database 106 via network 108. Although, the care receiver 114(1) may include any number of care providers 124(1)-124(n) in the trusted care providers list. The account profiles for care receivers 114(1)-114(n) may further be customized by care receivers 114(1)-114(n) to include how they prefer to receive communications from care providers 124(1)-124(n), which may include associating one or more communication platforms corresponding with each of the care providers 124(1)-124(n), ranking of communication platforms by care receivers 114(1)-114(n), when care receivers 114(1)-114(n) would prefer to receive communications from care providers 124(1)-124(n) and customizing types of messages received from care providers 124(1)-124(n), although other customizations to receive communications by care receivers 114(1)-114(n) may also be included. This is further explained in detail below.

As described herein, a communication platform may include, for example, a web browser, text messaging applications such as short messaging services (SMS) messaging application or other native messaging applications, video calling applications, audio call applications, interactive voice applications such as IVR, or social networking applications such as Skype, Facebook messenger, Whatsapp, or the like. In some embodiments, the communication platform is native to the communication device. In some embodiments, the communication platform must be downloaded from an external source. In some embodiments, the communication platform may include a combination of native and downloaded software.

Associating by the care receivers 114(1)-114(n) one or more communication platforms with each of a corresponding care providers 124(1)-124(n) is further explained, by way of example, when a care receiver 114(1) associates a communication platform, such as an SMS messaging application with care provider 124(1), then all communications received from care provider 124(1) and exchanged between care provider 124(1) and care receiver 114(1) would be over the SMS messaging application. In another example, when a care receiver 114(1) associates web browser application and social networking applications with care provider 124(2), then all communications received from care provider 124(2) and exchanged between care provider 124(2) and care receiver 114(1) would be over the web browser application and social networking application. Although any number of communication platforms may also be associated with each of a corresponding care providers 124(1)-124(n).

Further the care receivers 114(1)-114(n) may also rank the communication platforms in an order of their communication, by way of example, when a care receiver 114(1) may assign a rank 1 to web browser application and rank 2 to social networking applications with care provider 124(2), then communications received from care provides 124(2) would be first communicated over to the web browser application that is assigned rank 1 associated with care receiver 114(1) and if there is no response received from the care receiver 114(1) then the communications received from care provider 124(2) would be transmitted over to the social networking application assigned rank 2. Although any number of communication platforms may also be ranked based on the care receivers 114(1)-114(n) preferences.

Further, the care receivers 114(1)-114(n) may also define when care receivers 114(1)-114(n) would prefer to receive communications from care providers 124(1)-124(n). Care receivers 114(1)-114(n) may define what time and/or date they would prefer to receive communications from care providers 124(1)-124(n). By way of example, care receiver 114(1) may customize their account profiles to select a date, by way of example, Mar. 1, 2020 as the date when they prefer to receive communication from care providers 124(1)-124(n). In another example, care receiver 114(2) may customize their account profiles to select a time and date, by way of example, 10:00 am on Apr. 1, 2020 as the date when they prefer to receive communication from care providers 124(1)-124(n). Although any other time and/or date may also be included by the care receivers 114(1)-114(n).

Further, types of messages received from care providers 124(1)-124(n), may include a follow up message on how care receivers 114(1)-114(n) are reacting to a prescribed medicine, a follow up message to schedule a checkup appointment with care receivers 114(1)-114(n), or to check care receivers care receivers' 114(1)-114(n) health, although any other type of messages communicated between care receivers 114(1)-114(n) and care providers 124(1)-124(n) may also be included.

Customizing types of messages received from care providers 124(1)-124(n) is defined by care receivers 114(1)-114(n), by way of example, care receiver 114(1) may define that a follow up message to schedule a checkup appointment is the only type of message that they would prefer to receive. In this example, care receiver 114(1) would only receive follow up messages to schedule a checkup appointment from care providers 124(1)-124(n). Although any other type of message that is to be received from care providers 124(1)-124(n) may be defined by the care receivers 114(1)-114(n).

In another example, the care providers 124(1)-124(n) may also define when to send communications to care receivers 114(1)-114(n). Care providers 124(1)-124(n) define what time and/or date would they prefer to send communication to care receivers 114(1)-114(n), by way of example, care provider 124(1) customizes their account profiles at the database 106 to select a date, by way of example, Jun. 1, 2020 as the date when they prefer to send their communications to care receivers 114(1)-114(n). In another example, care provider 114(2) may customize their account profiles to select a time and date, by way of example, 10:00 am on Nov. 1, 2020 as the date when they prefer to send communication to care receivers 114(1)-114(n). Although any other t e and/or date may also be included by the care providers 124(1)-124(n).

Healthcare provider server device 104 may be configured to access from database 106, account profiles for care receivers 114(1)-114(n) associated with user devices 102(1)-102(n) and account profiles for care providers 124(1)-124(n) associated with user devices 103(1)-103(n). The account profiles for care receivers 114(1)-114(n) includes a trusted care providers list. Further, the account profile for care receivers 114(1)-114(n) and care providers 124(1)-124(n) includes account profile data.

In some embodiments, healthcare provider server device 104 may be configured to receive inputs and account profile data associated from user devices 102(1)-102(n), user devices 103(1)-103(n). More particularly, first care provider 124(1) may utilize a user interface displayed on user device 103(1) to provide account profile data which is received and processed by the healthcare provider server device 104. Further, first care receiver 114(1) may utilize a user interface displayed on user device 102(1) to provide account profile data which is received and processed by the healthcare provider server device 104 for seamlessly switching between communication platforms.

Database 106 of system 100 may be communicatively coupled to healthcare provider server device 104 and user devices 102(1)-102(n), user device 103(1)-103(n) via network 108. Database 106 may include one or more memory devices that store information and are accessed and/or managed by one or more components of system 100. By way of example, database 110 may include Oracle™ databases, Sybase™ databases, or other relational databases or nonrelational databases, such as Hadoop sequence files, HBase, or Cassandra. Database 106 may include computing components (e.g., database management system, database server, etc.) configured to receive and process requests for data stored in memory devices of database 106 and to provide data from database 106.

Database 106 is configured to store account profile data associated with care receivers 114(1)-114(n) and care providers 124(1)-124(n). Account profile data for care receivers 114(1)-114(n) may include medical history information, medical treatment plans, prescriptions, age, gender, name, address, phone number, communication preferences, device information, communication history, such as email or text messaging conversations, user account information, such as a username and login credentials, and other information associated with care receivers 114(1)-114(n). Similarly, account profile data for care providers 124(1)-124(n) may include user account information, email history, or text messages communicated between care providers 124(1)-124(n) and care receivers 114(1)-114(n). User account information stored in account profile data for care providers 124(1)-124(n) includes care receivers 114(1)-114(n) name, phone number, address, communication preferences, email history, medical history, and emergency contact information, although any other information associated with care receivers 114(1)-114(n) may also be included. In this example, healthcare provider server device 104 identifies account profiles associated with care receiver 114(2) and care receiver 114(n) to be associated with care receiver 114(1). By way of example, the medical history associated with care receivers 114(1)-114(n) may include all of their previous doctor visits, x-rays files, health reports, previous surgeries, past health related information, historical data relating to body vitals such as blood pressure, body temperature, body weight, blood sugar, although any other patient health information may be included. As another example, the communication history may include any communications communicated to or from care receivers 114(1)-114(n). For example, the email history may include emails communicated to or from care receivers 114(1)-114(n), including emails communication between care receivers 114(1)-114(n) and care providers 124(1)-124(n). As a further example, the text messages may include text messages to or from care receivers 114(1)-114(n), including text messages communicated between care receivers 114(1)-114(n) and care providers 124(1)-124(n). In some embodiments, care receivers 114(1)-114(n) may configure their account profiles to include information relating to their preferred communication platform or device information, as explained above.

In one aspect, healthcare provider server device 104 may include one or more computing devices, configured to perform one or more operations consistent with disclosed embodiments, as described more fully below in relation to FIG. 3. In one aspect, healthcare provider server device 104 may include one or more servers or server systems. Healthcare provider server device 104 may include one or more processors configured to execute software instructions stored in a memory or other storage device. The one or more processors may be configured to execute the stored software instructions to perform Internet-related communication, and health service-based processes. Healthcare provider server device 104 may be operated by a healthcare provider or other third party. For example, this may include a third party authorized by a healthcare provider to operate the server device. The one or more computing devices of healthcare provider server device 104 may also be configured to communicate with other components of system 100 to seamlessly switching between communication platforms. In some embodiments, healthcare provider server device 104 may provide one or more communication platforms (e.g. texting messaging services, social networking applications, web-sites or online portals) that are accessible by user devices 102(1)-102(n) and user devices 103(1)-103(n) over network 108. The disclosed embodiments are not limited to any particular configuration of healthcare provider server device 104.

Healthcare provider server device 104, user devices 102(1)-102(n) and user devices 103(1)-103(n) may be configured to communicate with each other over network 108. Network 108 may comprise any type of computer networking arrangement configured to provide communications or exchange data, or both, between components of system 100. For example, network 108 may include any type of network (including infrastructure) that provides communications, exchanges information, and/or facilitates the exchange of information, such as the Internet, a private data network, a virtual private network using a public network, a LAN or WAN network, a W Fi™ network, and/or other suitable connections that may enable information exchange among various components of system 100. Network 108 may also include a public switched telephone network ("PSTN") and/or a wireless cellular network. Network 108 may be a secured network or unsecured network. In some embodiments, one or more components of system 100 may communicate directly through a dedicated communication link(s).

User devices 102(1)-102(n) and user devices 103(1)-103(n) may be one or more computing devices configured to perform one or more operations consistent with the disclosed embodiments, as described more fully below in relation to FIG. 2. User devices 102(1)-102(n) and user devices 103(1)-103(n) may execute browser or related mobile display software that displays account profiles and interfaces for accessing medical record data, on a display included in, or connected to, user devices 102(1)-102(n) and user devices 103(1)-103(n), User devices 102(1)-102(n) and user devices 103(1)-103(n) may also store and execute mobile applications that allow care receivers 114(1)-114(n) and care providers 124(1)-124(n) to communicate with healthcare provider server device 104 to enable switching between multiple communication platforms.

It is to be understood that the configuration of the functional blocks of system 100 has been defined herein for convenience of description. The components and arrangement of the components included in system 100 may vary. For example, in some embodiments, system 100 may include other components that perform or assist in the performance of one or more processes consistent with disclosed methods. System 100 includes a number of components generally described as computing devices. Each of the computing devices may include any number of computing components particularly configured as a special purpose computing device to perform the functionality disclosed herein. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Figure 2:
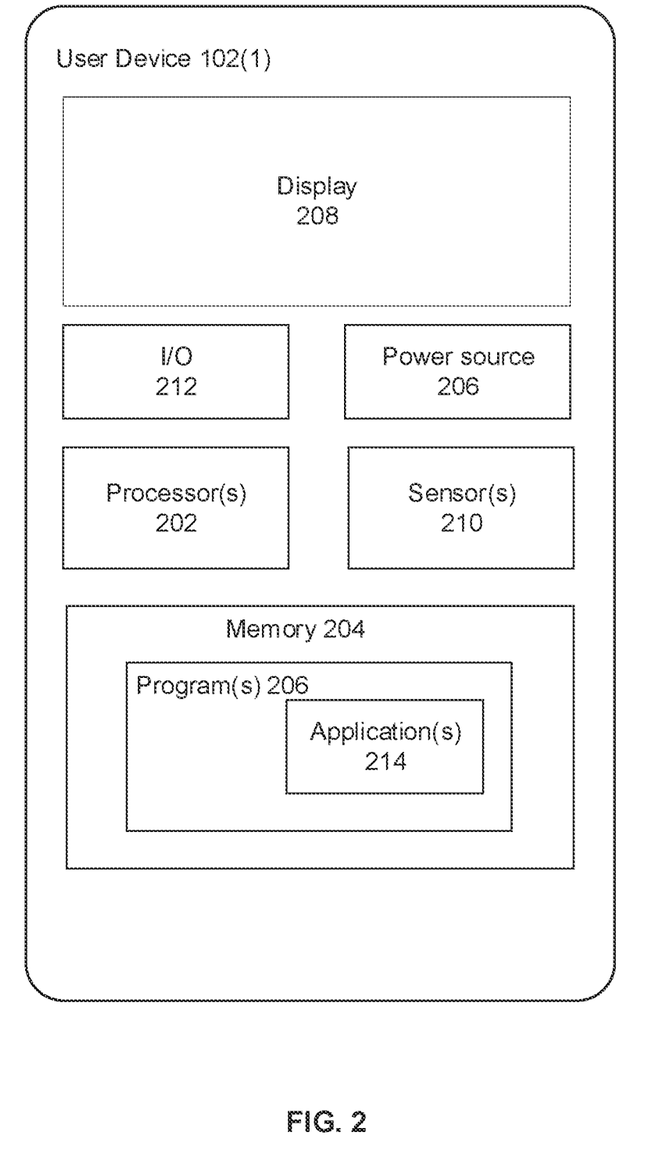
FIG. 2 is a block diagram of an exemplary user device, consistent with disclosed embodiments.

FIG. 2 is a block diagram of an exemplary user device 102(1), consistent with disclosed embodiments. User devices 102(2)-102(n) and user devices 103(1)-103(n) may be similarly configured, User device 102(1) may enable associated care receiver 114(1) to perform interactions with communication platforms with healthcare provider server device 104, for example, or receive information from healthcare provider server device 104. In some embodiments, user device 102(1) may be a personal computing device. For example, user device 102(1) may be a smartphone, a laptop or notebook computer, a tablet, a multifunctional watch, a pair of multifunctional glasses, or any mobile or wearable device with computing ability, or any combination of these computers and/or affiliated components.

User device 102(1) includes one or more processors 202 configured to execute software instructions stored in memory, such as a memory 204. Memory 204 may store one or more software programs 206 that when executed by processor 202 perform known Internet-related communication, content display processes, and other interactive processes for care receiver 114(1). For instance, user device 102(1) may execute a browser or related mobile display software that generates and displays interfaces including content on a display device 208 included in, or in communication with, user device 102(1). User device 102(1) may be a mobile device that executes mobile device applications and/or mobile device communication software, included in programs 206, that allows user device 102(1) to communicate with healthcare provider server device 104 and other components via network 108, to generate and display content in interfaces via display device 208. In some embodiments, the mobile device applications and/or mobile device communication software is native to the mobile device (i.e., does not require any software for download). In some embodiments, the mobile device applications and/or mobile device communication software are not native to the device and must be downloaded from an external source. In some embodiments, the mobile device applications and/or mobile device communication software are a combination of native and downloaded software. The disclosed embodiments are not limited to any particular configuration of user device 102(1). User device 102(1) may include any arrangement of one or more computing devices configured to perform one or more operations consistent with disclosed embodiments.

User device 102(1) may be configured to store, in memory 204, one or more operating systems that perform known operating system functions when executed by processor 202. By way of example, the operating systems may include Microsoft Windows™, Unix™, Linux™, Android™, Apple™ Mac OS operating systems, iOS, Chrome OS, or other types of operating systems. Accordingly, disclosed embodiments may operate and function with computer systems running any type of operating system. User device 102(1) may also include communication software stored in memory 204 that, when executed by processor 202, provides communications via network 108, such as Web browser software, tablet or smart handheld device networking software, etc.

Display device 208 may include, for example, a liquid crystal display (LCD), a light emitting diode screen (LED), an organic light emitting diode screen (OLED), a touch screen, and other known display devices. Display device 208 may display various information to care receiver 114(1). For example, display device 208 may display an interactive interface to care receiver 114(1) enabling care receiver 114(1) to operate user devices 102(1) to perform certain aspects of the disclosed methods. Display device 208 may display touchable or selectable options for care receiver 114(1) to select and may receive selection of options through a touch screen.

User device 102(1) includes I/O devices 212 that allow user device 102(1) to send and receive information or interact with care receiver 114(1) or another device. For example, I/O devices 212 may include various input/output devices, such as a keyboard, a mouse-type device, a gesture sensor, an action sensor, a physical button, switch, microphone, touchscreen panel, stylus, etc., that may be manipulated by care receiver 114(1) to input information using user devices 102(1). 110 devices 212 may also include an audio output device, such as a speaker configured to provide sound and audio feedback to care receiver 114(1) operating user device 102(1). In some embodiments, I/O devices 212 may include a light emitting component, such as LED or other component capable of providing a visible signal to care receiver 114(1). I/O devices 212 may also include haptic output devices, to provide haptic feedback to care receiver 114(1). I/O devices 212 may also include one or more communication modules (r of shown) for sending and receiving information from other components of system 100 by, for example, establishing wired or wireless connectivity between user device 102(1) and network 108. I/O devices 212 may include radio frequency, infrared, or other near-field communication interfaces, for communicating with other devices associated with network 108 or care receiver 114(1). Exemplary communication modules of I/O devices 212 may include, for example, a short-range or near field wireless communication modem, a Wi-Fi™ communication modem, or a cellular communication modem. I/O devices 212 may include a transceiver or transmitter configured to communicate using one or more wireless technologies/protocols that may include, without limitation, cellular (e.g., 3G, 4G, etc.) technology, Wi-Fi™ hotspot technology, RFID, near-field communication (NFC) or BLUETOOTH® technologies, etc. More generally, any uni- or bi-directional communication technology known to one of ordinary skill in the art may be implemented in user device 102(1) to exchange information with healthcare provider server device 104 or database 106 via network 108.

As described above, user devices 102(1) may be a device that executes mobile applications for performing operations consistent with disclosed embodiments. Thus, in some embodiments, programs 206 stored on user device 102(1) may include one or more software applications 214 installed thereon, that enable user device 102(1) to communicate with healthcare provider server device 104 via network 108 and perform aspects of the disclosed methods. For example, user device 102(1) may connect to healthcare provider server device 104 by using browser software to access and receive information or perform other operations associated with an internet service provider.

According to an exemplary embodiment, software applications 214 associated with healthcare provider server device 104 may be installed on user device 102(1), as shown in FIG. 2. For example, healthcare provider server device 104 may receive a request from user device 102(1) to download one or more software applications 214 to user device 102(1). In one embodiment, healthcare provider server device 104 may receive the request from care receiver 114(1), using a web browser application installed on user device 102(1). In another embodiment, healthcare provider server device 104 may receive the request to download one or more software applications 214 associated with healthcare provider server device 104 onto user device 102(1) from a webpage or another portal associated with healthcare provider server device 104 accessed by care receiver 114(1) via, e.g., user device 102(1). In this embodiment, healthcare provider server device 104 may store software instructions corresponding to one or more software applications 214 in database 106. For responding to the download request, healthcare provider server device 104 may receive additional information from user device 102(1) regarding the particular device specifications of user device 102(1) to enable user device 102(1) to download software instructions corresponding to the particular specifications. Alternatively, healthcare provider server device 104 may push a download request link to user device 102(1) or transmit software code corresponding to one or more software applications 214 directly to user device 102(1) in, for example, an e-mail, a text or short message service (SMS) message, a prompt through an app, or other suitable method. User device 102(1) may receive the software code related to one or more software applications 214, such as via network 108, to download and install the software code. Further, FIG. 2 shows a power source 212. The power source 212 is utilized to turn on and turn off the user device 102(1).

Figure 3:
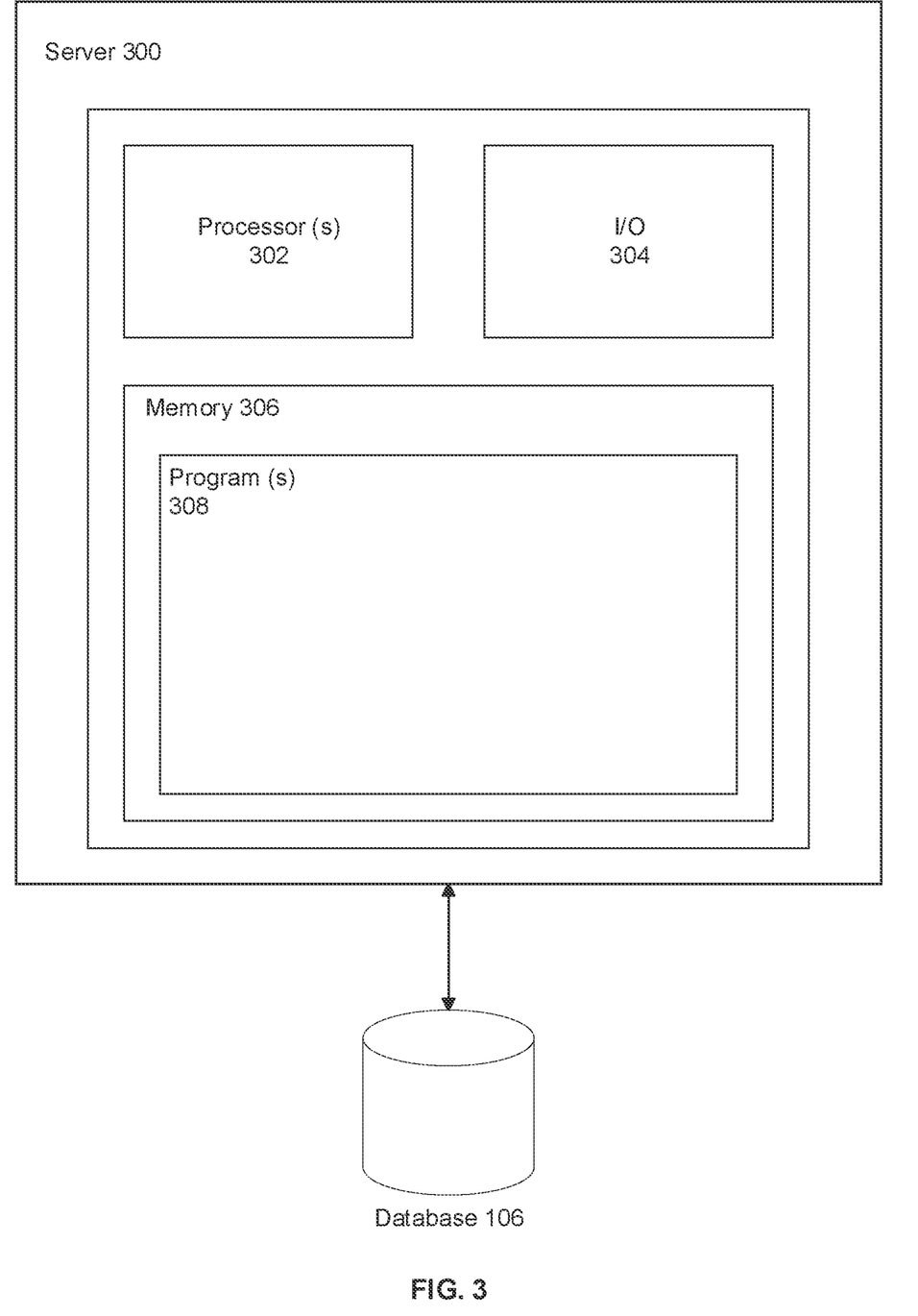
FIG. 3 is a block diagram of an exemplary server system, consistent with disclosed embodiments.

FIG. 3 shows an exemplary server 300 consistent with the disclosed embodiments. Variations of exemplary server 300 may constitute one or ore components of healthcare provider server device 104. In some embodiments, a third-party service provider server device (not shown in drawings) may communicate and transfer data with server 300. Third-party service provider server device may perform functions of healthcare provider server device 104. In one embodiment, server 300 includes one or more processors 302, one or more input/output (I/O) devices 304, and one or more memories 306. In some embodiments, server 300 may be a part of healthcare provider server device 104. In some embodiments, server 300 may take the form of a specially programmed server or computing system used by healthcare provider server device 104. In some embodiments, server 300 may be configured as an apparatus, embedded system, dedicated circuit, or the like based on the storage, execution, and/or implementation of software instructions that perform one or more operations consistent with the disclosed embodiments.

Processor 302 may include one or more known processing devices, such as a microprocessor from the Pentium™ or Xeon™ family manufactured by Intel™, or the Turion™ family manufactured by AMD™, for example. The disclosed embodiments are not limited to any type of processor(s) otherwise configured to meet the computing demands required of different components of system 100.

Input/output (I/O) devices 304 may include various input/output devices, such as a keyboard, a mouse-type device, a physical button, switch, etc., that may be manipulated by care receivers 114(1)-114(n) and/or care providers 124(1)-124(n) to input information using user devices 102(1)-102(n) and user devices 103(1)-103(n) respectively. I/O devices 304 may also include an audio output device. Exemplary communication modules of I/O devices 304 may include, for example, a short-range or near field wireless communication modem, a Wi-Fi™ communication modem, or a cellular communication modem. I/O devices 304 may include a transceiver or transmitter configured to communicate using one or more wireless technologies/protocols that may include, without limitation, cellular (e.g., 3G, 4G, etc.) technology, Wi-Fi™ hotspot technology, RFID, near-field communication (NFC) or BLUETOOTH® technologies, etc. More generally, any uni- or bi-directional communication technology known to one of ordinary skill in the art may be implemented in healthcare provider server device 104, user devices 102(1)-102(n), user devices 103(1)-103(n) or database 106 via network 108.

Memory 306 may include one or more storage devices configured to store instructions used by processor 302 to perform functions related to disclosed embodiments. For example, memory 306 may be configured with one or more software instructions, such as program(s) 308 that perform one or more operations when executed by processor 302. The disclosed embodiments are not limited to separate programs or computers configured to perform dedicated tasks. For example, memory 306 may include a single program 308 that performs the functions of server 300, or program 308 may comprise multiple programs. In certain embodiments, memory 306 may store sets of instructions or programs 308 for switching between a plurality of communication portals. These sets of instructions may be executed by processor 302 to perform communication and/or processes consistent with disclosed embodiments.

Figure 4A:
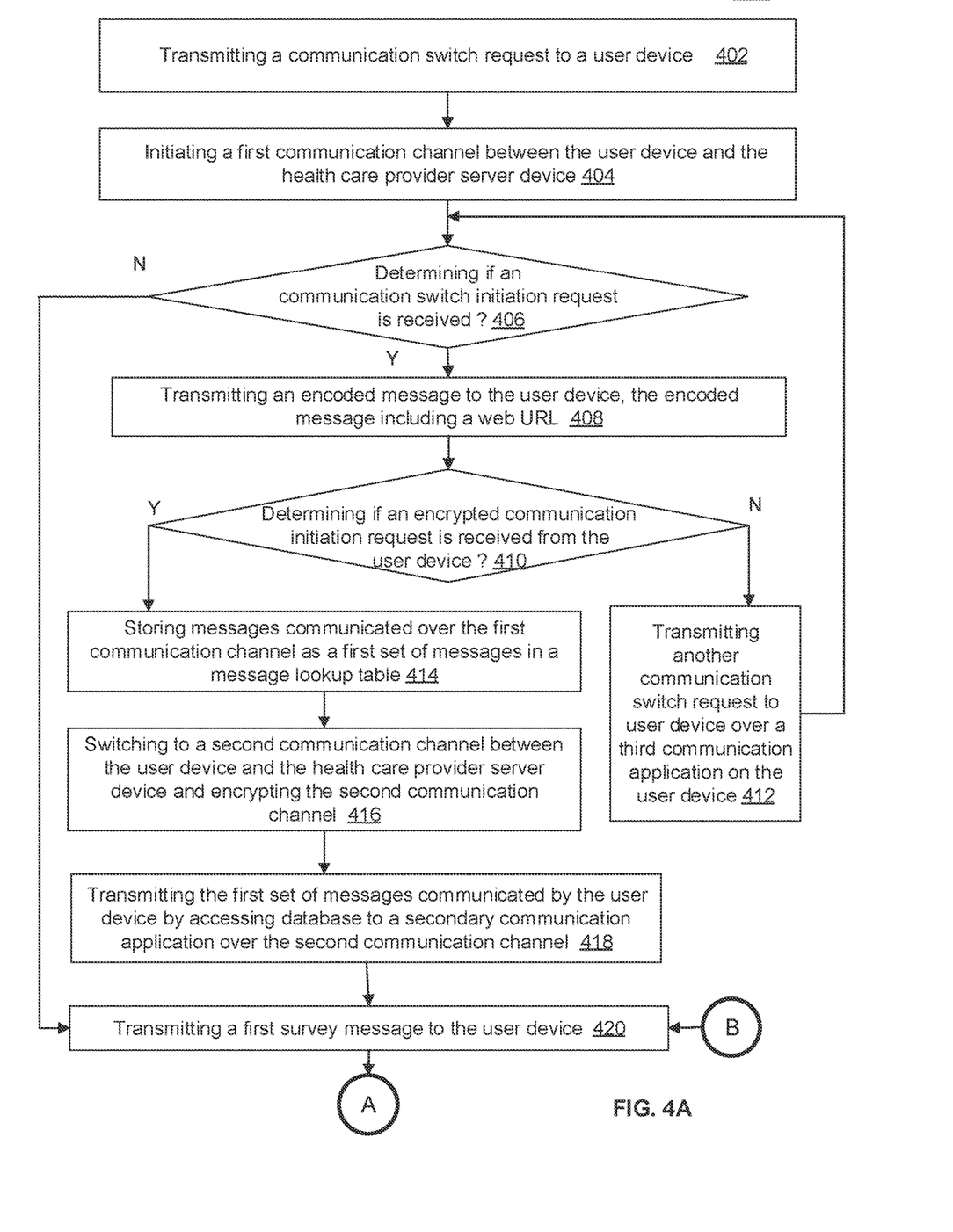
FIGS. 4A-4B contain a flowchart of an exemplary process of systems and methods for switching between communication channels using secure healthcare communication system, consistent with disclosed embodiments.

Exemplary process 400 for switching between communication platforms using secure healthcare communication system, consistent with the disclosed embodiments, is described next with reference to FIGS. 4A-4B. In certain aspects, healthcare provider server device 104 utilizes server 300 to execute software instructions that perform one or more of the operations of process 400. Also, server 300 may perform all of the functions of healthcare provider server device 104.

Figure 4B:
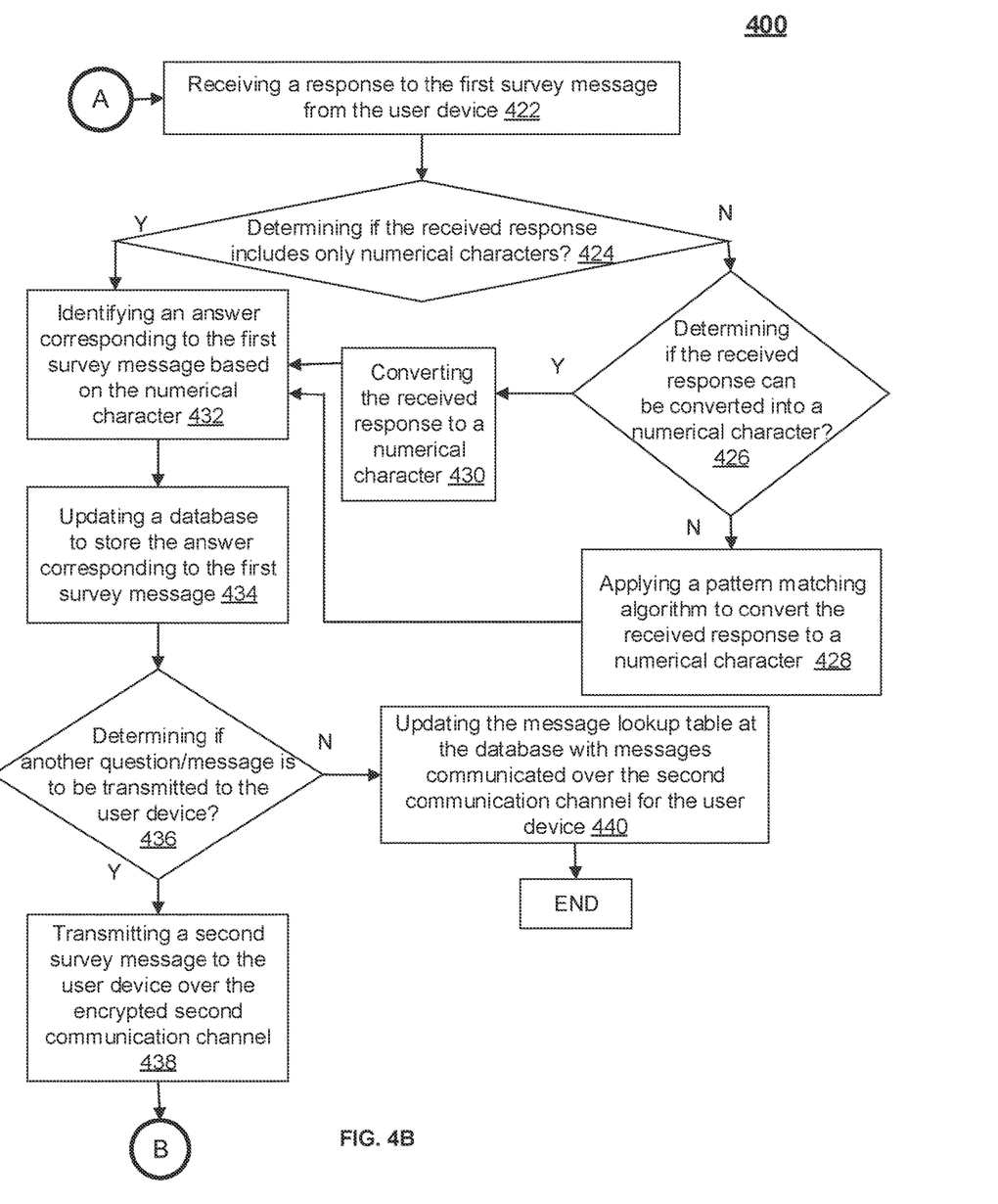
Figure 5A:
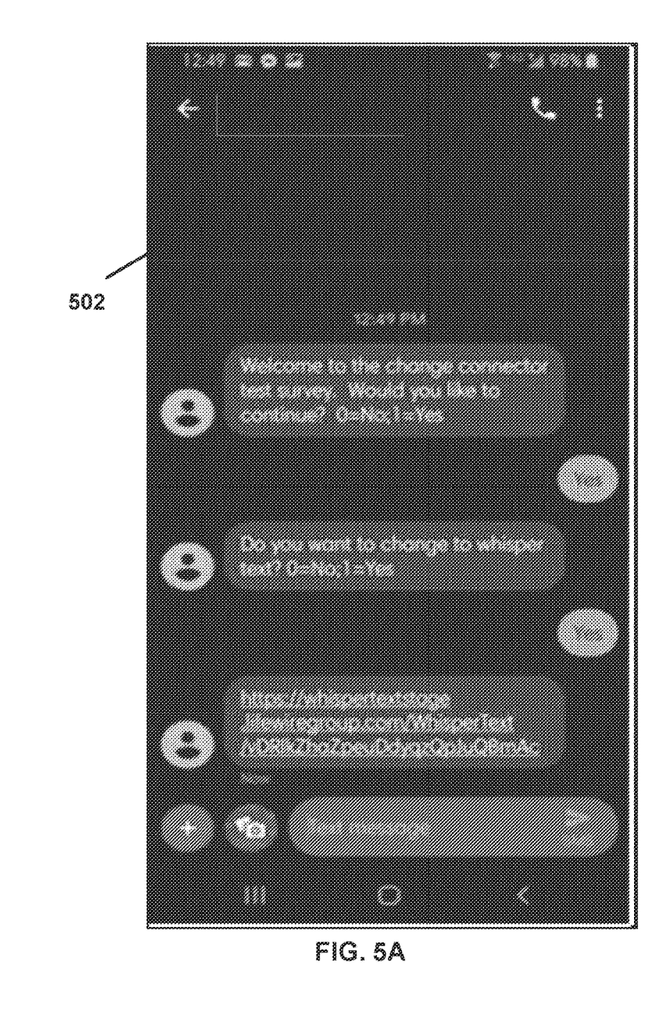
FIGS. 5A-5B provide diagrammatic representations of an exemplary system, consistent with disclosed embodiments.
Figure 5B:
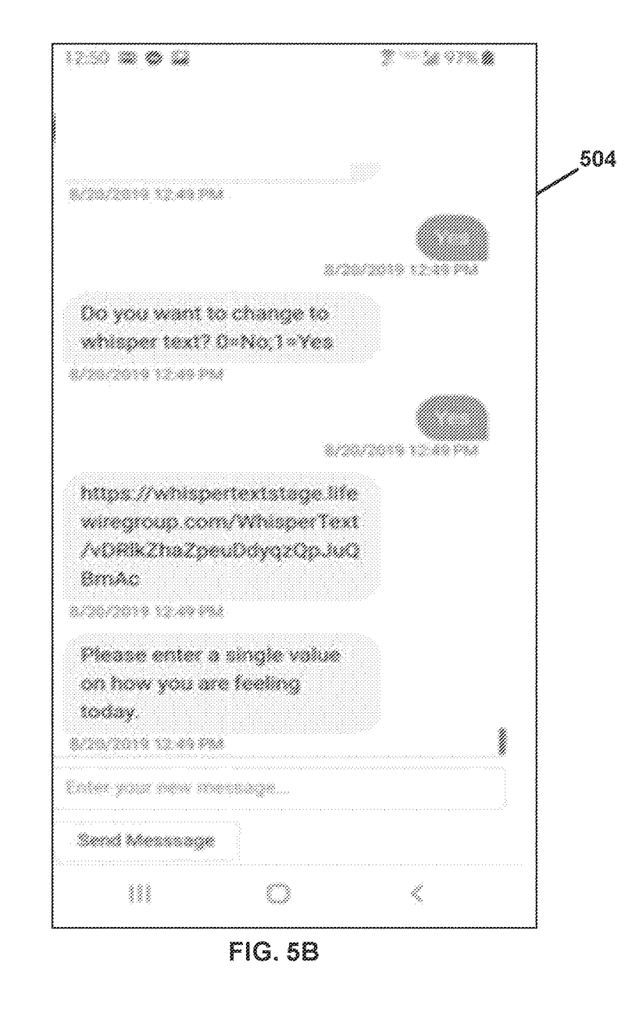

FIG. 5A that illustrates a short message service (SMS) application 502 on user device 102(1) utilized to communicate with healthcare provider server device 104; and FIG. 5B that illustrates a secondary communication application 504 (e.g. a web browser application, audio calling application, video calling application, social networking application, etc) on user device 102(1) utilized to communicate with healthcare provider server device 104. Accordingly, FIGS. 5A-5B consistent with the disclosed embodiments are described along with the description of FIGS. 4A-4B, Healthcare provider server device 104 in step 402 transmits a communication switch request to user device 102(1) associated care receiver 114(1). Healthcare provider server device 104 may transmit the communication switch request automatically to care receivers 114(1)-114(n) based on pre-defined rules without receiving care request of step 402. Pre-defined rules may include transmitting the communication switch request at a schedule of every 6 hours, to check on, by way of example, care receiver 114(1) to ask whether care receiver 114(1) has takes their medication, that is to be take every 6 hours.

In some embodiments, the switch request may be received from user device 102(1) associated with care receiver 114(1). By way of example, care receiver 114(1) may send a communication, such as a text message containing the term "whispertext" to healthcare provider server device 104. The text message may also be sent during the communication exchange between a care receiver and healthcare provider server device 104. In another embodiment, care receiver 114(1) may send an email, wherein the email may include a text of "whispertext" in the subject line and/or body of the email.

In this example, communication switch request is a text message that displays a prompt to the care receiver 114(1), asking the care receiver 114(1) one or more queries. For example, the message may request user to answer a survey to answer follow up health questions provided by their care provider 124(1) (e.g. doctor). By way of example, the communication switch request may include a text message that may read "Welcome to the survey. Would you like to switch your communication platform? 0=NO; 1=YES". If the care receiver 114(1) participates in the survey, they may provide an input by utilizing user device 102(1), by entering a number 1 to continue with the survey by switching the communication platform or by entering a number 0 to end the survey. When the care receiver 114(1) inputs number 0 as an Input the survey ends and the method ends here. However, when the care receiver 114(1) inputs number 1 then the method proceeds to step 406. In some embodiments, a survey includes one or more queries relating to the care receiver. For example, a survey may include a query such as "Please enter a single value on how your are feeling today," as shown in FIG. 5B.

FIG. 5A discloses another example of the text message that the communication switch request and may read "Welcome to the change connector test survey. Would you like to continue? 0=No; 1=Yes". If the care receiver 114(1) is interested in participating in the survey, they may provide an input by utilizing user device 102(1), by entering a number 1 to continue with the survey by switching the communication platform or by entering a number 0 to end the survey. When the care receiver 114(1) inputs number 0 as an input the survey ends and the method ends here.

In another embodiment, the communication switch request may include a text message that may read "Welcome to a follow up survey. Would you like to continue? 0=NO; 1=YES". If the care receiver 114(1) is interested in participating in the survey, they may provide an input by utilizing user device 102(1), by entering a number 1 to continue with the survey or by entering a number 0 to end the survey. When the care receiver 114(1) inputs number 0 as an input the survey ends and the method ends here. However, when the care receiver 114(1) inputs number 1 then the healthcare provider server device 104 may transmit a text message that may read "Welcome to a follow up survey. Would you like to switch your communication platform? 0=NO; 1=YES". If the care receiver 114(1) is interested in participating in the survey, they may provide an input by utilizing user device 102(1), by entering a number 1 to continue with the survey by switching the communication platform or by entering a number 0 to end the survey. When the care receiver 114(1) inputs number 0 as an input the survey ends and the method ends here. However, when the care receiver 114(1) inputs number 1 then the method proceeds to step 406.

In another embodiment, healthcare provider server device 104 in step 402 receives a care request from care providers 124(1)-124(n) via their associated user devices 103(1)-103(n). By way of example, care provider 124(1) (e.g. a doctor) may utilize a health care mobile application installed on user device 103(1) to follow up with a care receiver 114(1) (e.g. a patient) to get updates on their health. Care provider 124(1) interacts with an interface on the health care mobile application that causes to generate and transmit the care request to the healthcare provider server device 104 to follow up with a care receiver 114(1) (e.g. a patient) to get updates on their health. The interaction with the health care mobile application may include clicking of an icon or touching of an icon on the health care mobile application. The care request includes an identifier associated with user device 102(1) of care receiver 114(1) with whom the care provider 124(1) wishes to follow up. The identifier associated with user device 102(1) of care receiver 114(1) may include an internet protocol (IP) address of user device 102(1), a username associated with account profile data of care receiver 114(1), or phone number of user device 102(1), although any other identifier may also be included.

In some embodiments, care provider 124(1) (e.g. a doctor) may utilize an application native to the user device (i.e., that does not require downloading software from an external source), for example a web browser application that may be native to user device 103(1) to access a website to follow up with a care receiver 114(1) (e.g. a patient) to get updates on their health. Care provider 124(1) interacts with an interface on the website that causes to generate and transmit the care requests to the healthcare provider server device 104 to follow up with a care receiver 114(1) (e.g. a patient) to get updates on their health. In some embodiments, care receivers 114(1)-114(n) associated with corresponding user devices 102(1)-102(n) may utilize an application, such as a web browser application or text messaging application, native to user devices 102(1)-102(n) to communicate with care receivers 114(1)-114(n). This enables using native applications to the device, including accessing a web browser application, to exchange messages without requiring the downloading of applications, to exchange communications between care receivers 114(1)-114(n) and care providers 124(1)-124(n). Accordingly, the disclosed system/method provides technical advantages and solves real-world, practical problems. For example, the disclosed technology may be by utilized by devices that do not support installing external applications. As another example, the disclosed technology solves the aforementioned problems by enabling easier access without requiring installation of third party or external software applications on a shared device, which may itself include limited privileges to the user. As yet another example, the disclosed technology provides advantages of saving device memory, by not requiring the installing of dedicated applications and storing historical data and profile data on the server rather than the device.

The communication switch request may be generated in response to a care request received from a care provider 124(1)-124(n) via their associated user devices 103(1)-103 (n). Upon receiving of the care request by healthcare provider server device 104, healthcare provider server device 104 identifies user device 102(1) associated with care receiver 114(1) based on the received identifier. Upon identifying user device 102(1), healthcare provider server device 104 transmits a communication switch request to user device 102(1). Healthcare provider server device 104 transmits the communication switch request over a first communication platform. In this example, first communication platform is a short messaging service (SMS) application, and the communication switch request is transmitted as a SMS to the user device 102(1). However, the first communication platform may also include websites on a web browser, an interactive voice recognition (IVR) application, social networking applications on mobile devices or computers, although any other communication software may also be included.

In another embodiment, healthcare provider server device 104 may transmit the communication switch request automatically to care receivers 114(1)-114(n) based on care receivers 114(1)-114(n) preferences stored in account profiles at the database 106 without receiving care request of 402.

The account profiles for care receivers 114(1)-114(n) may include how they prefer to receive communications from care providers 124(1)-124(n), which may include when care receivers 114(1)-114(n) would prefer to receive communications from care providers 124(1)-124(n).

Healthcare provider server device 104 access database 106 to collect the care receiver 114(1)-114(n) preferences periodically and based on the preferences set by the care receiver 114(1)-114(n), healthcare provider server device 104 generates a care request. Healthcare provider server device 104 may access the database 106 every 2 minutes, every 1 hour, or every 6 months, although any number of time period may be included. Upon generation of the care request, healthcare provider server device 104 transmits a communication switch request as explained below in step 404.

By way of another example, when care receiver 114(1) customizes account profiles to select a time and date, by way of example, 10:00 am on Apr. 1, 2020 as the date when they prefer to receive communication from care providers 124 (1)-124(n), then healthcare provider server device 104 determines that it should initiate communication with care receiver 114(1) (e.g. by automatically transmitting a the communication switch request to care receiver 114(1)) at 10:00 am on Apr. 1, 2020.

In another embodiment, healthcare provider server device 104 may transmit the communication switch request automatically to care receivers 114(1)-114(n) based on care receivers 114(1)-114(n) preferences stored in account profiles at the database 106 upon receiving the care request of 402 from care providers 124(1)-124(2).

The account profiles for care receivers 114(1)-114(n) may further be customized by care receivers 114(1)-114(n) to include how they prefer to receive communications from care providers 124(1)-124(n), which may include associating one or more communication platforms corresponding with each of the care providers 124(1)-124(n), ranking of communication platforms by care receivers 114(1)-114(n).

By way of example, when a care receiver 114(1) associates a SMS messaging application with care provider 124 (1), then healthcare provider server device 104 determines that all communications received from care provider 124(1) and exchanged between care provider 124(1) and care receiver 114(1) would be over the SMS messaging and in response transits the communication switch request over the SMS messaging platform.

By way of another example, when a care receiver 114(1) may assign a rank 1 to web browser and rank 2 to social networking applications with care provider 124(2), then healthcare provider server device 104 determines that communications received from care provides 124(2) would be over first communicated to the web browser with assigned rank 1 associated with care receiver 114(1) and in response transmits the communication switch request over the web browser platform. Further, if there is no response received from the care receiver 114(1) then the communications received from care provides 124(2) would be transmitted over to the social networking application assigned rank 2 and in response transmits the communication switch request over the social networking application platform.

In another embodiment, the communication switch request may be generated in response to a care request received from one of a care receiver 114(1)-114(n) via their associated user devices 102(1)-102(n).

Healthcare provider server device 104 in step 404, upon receiving an input number 1 as a response from the user device 102(1) in response to the communication switch request in step 402, the health care provider server device 104, initiates a first communication channel between the user device 102(1) and healthcare provider server device 104. A first communication channel is network communication link that is established between the user device 102(1) and healthcare provider server device 104. This first communication channel is utilized by the user device 114(1) to communicate messages with the healthcare provider server device 104 over a SMS application installed on user device 102(1).

Healthcare provider server device 104 in step 406 determines if a communication switching initiation request is received from the user device 102(1) associated with the care receiver 114(1). By way of example, the communication switch request transmitted in step 404 may include a text message that may read "Welcome to a follow up survey. Would you Ike to switch your communication platform 0=NO; 1=YES". If the care receiver 114(1) is interested in participating in the survey, the care receiver 114(1) may provide an input by utilizing user device 102(1), to enter a number 1 to continue with the survey or by entering a number 0 to proceed to step 420 receive the survey messages without switching of the communication platform. When the care receiver 114(1) inputs number 0 as input, then the method takes the No branch and proceeds to step 420 here. However, when the care receiver 114(1) inputs number 1. When the healthcare provider server device 104 receives the response of number 1 from user device 102(1) then the healthcare provider server device 104 determines that the response received from the user device 102(1) to be a communication switching initiation request and the method takes the yes branch and proceeds to step 408.

FIG. 5A discloses another example of the text message that the communication switch request and may read "Do you want to change to whisper text? 0=No; 1=Yes", If the care receiver 114(1) is interested in participating in the survey, the care receiver 114(1) may provide an input by utilizing user device 102(1), to enter a number 1 to continue with the survey or by entering a number 0 to proceed to step 420 receive the survey messages without switching of the communication platform. When the care receiver 114(1) inputs number 0 as an input, then the method takes the No branch and proceeds to step 420 here. However, when the care receiver 114(1) inputs number 1. When the healthcare provider server device 104 receives the response of number 1 from user device 102(1) then the healthcare provider server device 104 determines that the response received from the user device 102(1) to be a communication switching initiation request and the method takes the yes branch and proceeds to step 408.

Next, healthcare provider server device 104 in step 408 transmits an encoded message to the first communication platform of the user device 102(1), the encoded message including a web URL 408. In this step healthcare provider server device 104 transmits a text message to the user device 102(1), the text message including an encoded interaction element. The encoded interaction element includes an identifier in the form of a website uniform resource locator (URL), a quick response (QR) code, or a barcode. By way of example, the encoded message may read "To switch communication please click the URL or link https://whispertextstage.lifewiregroup.com/vDRKZhaMNkL", as shown in FIG. 5A.

The identifier of the encoded interaction element is embedded with an identifier associated with a second communication platform. The identifier of the second communication platform includes a website address for a health service provider (e.g., a doctor, hospital, elderly nursing home, etc.) accessed over a web browser application, an URL address associated with a video calling applications, audio call applications or social networking applications such as Facebook messenger or Whatsapp, where the care receiver 114(1) may have an account. This second communication platform is utilized by the care receiver 114(1) to communicate with the care provider 124(1). Further, web browser application, video calling applications, audio call applications or social networking applications may also be referred to as secondary communication applications.

In another embodiment, when a quick response (OR) code or a barcode is included the encoded message, then the encoded message may read "To switch communication please scan the code".

Healthcare provider server device 104 in step 410 determines if an encrypted communication initiation request is received from the user device based on the encoded message. For example, the encrypted communication initiation request may be received in response to a user interaction with the encoded message. As another example, the encrypted communication initiation request may be received in response to an expiration of time after sending the encoded message. The response in step 410 is received from the user device and may be generated upon a user interaction with the identifier in the encoded message. User interaction with the encoded message may include clicking of the URL the identifier within the encoded message, scanning of the OR code, a barcode identifier, or some other embedded identifier within the encoded message. Encrypted communication initiation request is a request to healthcare provider server device 104 to terminate first communication channel established between the user device 102(1) and the healthcare provider server device 104 to communicated with the first communication platform (e.g. a SMS platform or an IVR application) and then establishing a second communication channel between the user device 102(1) and the healthcare provider server device 104 to communicate with a second communication platform (e.g. a web browser platform). Here, the second communication channel is an encrypted communication channel.

In this step, healthcare provider server device 104 determines if a response to the encoded message sent in the previous step 408 is received from the user device 102(1). By way of example, when the encoded message sent in step 408 reads "To switch communication please click the URL or link https://whispertextstage.lifewiregroup.com/vDRKZhaMNkL", then healthcare provider server device 104 determines if care receiver 114(1) associated with user device 102(1) has interacted with the link (e.g. clicked on the link) in the encoded message. When the care receiver 114(1) does not click on the link, then healthcare provider server device 104 determines that an encrypted communication initiation request is not received from the user device 102(1) and the method takes the no branch and proceeds to step 412. Step 412 is explained in detail later below.

Back in step 410, when the care receiver 114(1) clicks on the link, then healthcare provider server device 104 determines that an encrypted communication initiation request is received from the user device 102(1) as a response and the method takes the yes branch and proceeds to step 414.

Healthcare provider server device 104 in step 414 stores all of the messages communicated between the user device 102(1) and the healthcare provider server device 104 in database 106 as a first set of messages, and the method proceeds to step 416. The first set of messages communicated by user device 102(1) are stored with a corresponding identifier of the user device 102(1) in database 106 as part of a message lookup table. Identifier of the user device 102(1) may include, an Internet protocol (IP) address of user device 102(1), a username associated with account profile data of care receiver 114(1), or phone number of user device 102(1), although any other identifier may also be included.

Healthcare provider server device 104 in step 416 switches to a second communication channel between the user device 102(1) and the healthcare provider server device 104 to communicate with the second communication platform and performs encryption of the second communication channel. Upon determining that an encrypted communication initiation request is received from user device 102(1), healthcare provider server device 104 terminates its first communication channel established between the user device 102(1) and the healthcare provider server device 104 over the first communication platform (e.g. a SMS platform). Upon terminating the first communication channel, healthcare provider server device establishes a second communication channel between the user device 102(1) and the healthcare provider server device 104 to communicate with the second communication platform. However, the second communication platform may also include SMS applications, text messaging applications, an interactive voice recognition (IVR) application, social networking applications on mobile devices or computers, although any other communication software may also be included. Upon establishing the second communication channel, healthcare provider server device 104 encrypts the second communication channel. Encrypting of second communication channel is performed using by way of example, secure hash algorithms and/or cryptographic hash functions, however any other encrypting algorithm may also be utilized.

FIG. 5B shows a secondary communication application 504 on user device 102(1) utilized to communicate with healthcare provider server device 104 upon switching to a second communication channel from a first communication channel to communicate with the second communication platform. In this example, secondary communication application 504 is a website for a health service provider.

Healthcare provider server device 104 in step 418 retrieves previously stored first set of messages associated with an identifier corresponding to user device 102(1) by accessing message lookup table stored in the database 106. By way of example, for user device 102(1) since the first set of messages are communicated over the first communication channel and previously stored at step 414 in the message lookup table at the database 106, only those first set of messages that are communicated over the first communication channel on the first communication platform will be retrieved from the database 106. Upon retrieving the first set of messages, the healthcare provider server device 104 sends the first set of messages communicated over the first communication channel to the user device 102(1) to be displayed on the user device 102(1).

Healthcare provider server device 104 in step 420 transmits a first survey message to the user device 102(1) over the encrypted second communication channel established in step 416. The first survey message is displayed after displaying the first set of messages retrieved from database 106 in step 418. By displaying first set of messages retrieved in step 418, the care receivers 114(1) are provided with an optimized process viewing their previous communications that were performed on different communication platforms at a single interface. The first survey message may read "Please enter a single value on you are feeling better today? 1=Yes; 2=No; 3=Great". Further, in some embodiments, first survey message may be any type of message communicated to the user device 102(1), including, for example, follow up messages relating to how care receivers 114(1)-114(n) are reacting to a prescribed medicine, follow up messages to schedule a checkup appointment with care receivers 114(1)-114(n), messages relating to general feedback, or to check care receivers' 114(1)-114(n) health, although any other type of messages communicated between care receivers 114(1)-114(n) and care providers 124(1)-124(n).

Healthcare provider server device 104 in step 422 of FIG. 4B receives a response to the first survey message from the user device 102(1). The response received in step 422 may be an answer response from the user device 102(1) in response to the first survey message transmitted to the user device 102(1). By way of example, for the first survey message that reads "Please enter a single value on you are feeling better today? 1=Yes; 2=No; 3=Great", the user device 102(1) associated with the care receiver 114(1) may provide answer response by using their user device 102(1) as an answer to the survey message. This answer response received by the healthcare provider server device 104 as a response from user device 102(1) may include numerical characters, alphabetical characters, or alphanumeric characters, although any other type of response may also be included. Numerical characters may include 1, 2 or 3, although any other numerical values may also be included. Alphabetical characters may include one, two, y, ye, yes, or yeah, although any other alphabetical values may also be included. Alphanumerical characters may include, one 1, two 2, or three 3, although any other alphanumerical values may also be included. Upon receiving the answer response to the first survey message from the user device 102(1) then the method proceeds to step 424.

Healthcare provider server device 104 in step 424 analyzes the received answer response to determine if the answer response includes only numerical characters. Healthcare provider server device 104 may apply a previously programmed algorithm to determine if the answer response includes only numerical characters. By way of example, previously programmed algorithm may include a semantic processing algorithm, or any natural language processing algorithm to determine if the response includes only numerical characters. When the healthcare provider server device 104 determines that received answer response does not include only numerical characters then the method takes the no branch and proceeds to step 426.

Healthcare provider server device 104 in step 426 determines if the received answer response can be converted into a numerical character by applying previously programmed algorithm. In this step healthcare provider server device 104 determines if the received answer response is a spelling for a numerical character. By way of example, when the received answer response is "one", "two", or "three", then the healthcare provider server device 104 determines that received answer response of "one" is a spelling for a numerical character of "1" and can be converted into a numerical character, received response of "two" is a spelling for a numerical character of "2" and can be converted into a numerical character, or the received answer response of "three" is a spelling for a numerical character of "3" and can be converted into a numerical character, although any other number may also be included. In this example, when healthcare provider server device 104 determines that the received answer response is a spelling for a numerical character, then the method takes the yes branch and proceeds to step 430. Determining whether the received answer response includes one or more non-numerical characters includes determining that the answer response includes at least one alphabetical or other non-numerical character.

In another embodiment, healthcare provider server device 104 determines if the received response matches to a numerical character, by accessing a response lookup table stored in memory 306. Response lookup table may include a list of responses corresponding to a numerical character. Healthcare provider server device 104 identifies the received response in the list of responses in the response lookup table and then identifies a numerical character corresponding to the response. In this embodiment, upon identifying the response, the method will proceed to step 434.

Healthcare provider server device 104 in step 430 converts the received answer response into a numerical value. By way of example, when the received answer response is "one", "two", or "three", then the healthcare provider server device 104 applies the previously programmed algorithm and converts the received answer response of "one" into a numerical character of "1", converts the received answer response of "two" into a numerical character of "2", or converts the received answer response of "three" into a numerical character of "3", although any other number may also be included, then the method proceeds to step 432.

Back in step 426, when healthcare provider server device 104 applies the previously programmed algorithm to determine if the received answer response is not spelling for a numerical character, then the method takes the no branch and proceeds to step 428. By way of example, when the received answer response is "y", "ye", "yes", "yeah", "great", "grate", "tree", or "tee", then the healthcare provider server device 104 determines that received answer response is not spelling a numerical character and proceeds to step 428.

Healthcare provider server device 104 in step 428 applies a pattern matching algorithm to convert the received answer responses that are identified in step 426. In this example, the pattern matching algorithm is programmed to identify words that may be intended to correspond to "yes", such as "y", "ye", "yea", or "yeah", as well "yes" to be converted into numerical character 1, although any other words that correspond to yes may also be included. Further the pattern matching algorithm is programmed to identify words that may be intended to correspond to "No", such as "n", "ne", or "na", as well as "no" to be converted into numerical character 2, although any other words that correspond to no may also be included. Further the pattern matching algorithm is programmed to identify words that may be intended to correspond to "great", such as "gret", or "greet", as well "great" are to be converted into numerical character 3, although any other words that correspond to great may also be included. Further the pattern matching algorithm is programmed to identify words that may be intended to correspond to "one", "two", or "three", although any other words may also be included.

By way of example, when the received answer response is "y", "ye", "yes", "yeah", then the pattern matching algorithm identifies that the care receiver 114(1) must have implied to respond to the first survey message with 1 and converts the received answer response of "y", "ye", "yes", or "yeah" to numerical character 1. By way of another example, when the received answer response is "n", "ne", "a", or "no", then the pattern matching algorithm identifies that the care receiver 114(1) must have implied to respond to the first survey message with 2 and converts the received answer response of "n", "ne", "na", or "no" to numerical character 2. By way of another example, when the received answer response is "gret", or "graet", then the pattern matching algorithm identifies that the care receiver 114(1) must have implied to respond to the first survey message with 3 and converts the received answer response of "gret", or "graet" to numerical character 3, The method then proceeds to step 432.

Back in step 424, when the healthcare provider server device 104 determines that received answer response includes only numerical characters then the method takes the yes branch and proceeds to step 432.

Healthcare provider server device 104 in step 432, identifies a user response corresponding to the first survey message based on the numerical character determined in steps 424, 428, and 430. By way of example, when healthcare provider server device 104 determines that the first survey message includes the options of 1=Yes; 2=No; 3=Great, accordingly, based on the numerical characters identified in 424, 428, and 430, healthcare provider server device 104 associates Yes with the numerical character 1, No with the numerical character 2, or Great with the numerical character 3.

Healthcare provider server device 104 in step 434 updates a database to store the user response corresponding to the first survey message. By way of example, the user response identified in step 432 based on the answer response received from the user device 102(1) is stored with a corresponding identifier of the user device 102(1) in association with the first survey message in database 106 as part of a survey lookup table. Identifier of the user device 102(1) may include, an Internet protocol (IP) address of user device 12(1), a username associated with account profile data of care receiver 114(1), or phone number of user device 102(1), although any other identifier may also be included. the method then proceeds to step 436.

Healthcare provider server device 104 in step 436 determines if another survey message is to be transmitted to the user device 102(1). When healthcare provider server device 104 determines that another survey message is to be transmitted to the user device 102(1), then the method takes the yes branch and proceeds to step 438.

Healthcare provider server device 104 in step 438 transmits a second survey message to the user device 102(1) over the encrypted second communication channel and the method loops back to step 420.

When back in step 436 healthcare provider server device 104 determines that another survey message is not to be transmitted to the user device 102(1), then the method takes the no branch and proceeds to step 440.

Healthcare provider server device 104 in step 440 updates the message lookup table with messages communicated over the second communication channel for the user device 102(1). An entry corresponding with an identifier associated with user device 102(1) in the message lookup table is updated to include the messages communicated over the second communication channel and the method ends here.

Back in step 412, healthcare provider server device 104 establishes a third communication channel and transmits another communication switch request to user device 102(1) over a third communication platform on the user device 102(1) over the third communication channel established between the user device 102(1) and the healthcare provider server device 104. The third communication platform may include a social networking application, although any other application may also be included. the method then loops back to step 410. However, the third communication platform may also include websites on a web browser, SMS, texting messaging applications, although any other communication software may also be included In another embodiment, in step 418, when the user device 102(1) may have already participated in a previous survey and would have communicated over plurality communication platforms over the corresponding plurality of communication channels, then those first set of messages would also be retrieved in this step 418. By way of example, first set of messages communicated by the user device 102(1) over the first communication channel and second communication channel would be retrieved, although any number of first set of messages form a plurality of communication channels may also be included. First set of messages communicated by the user device 102(1) over the first communication channel would be retrieved from the message lookup table and first set of messages communicated by the user device 102(1) over the second communication channel would be retrieved from the survey lookup table. Further, the first set of messages form the first communication channel will be displayed first and the first set of messages form the second communication channel will be displayed second in a sequential order one after the other on the user device 102(1) in step 420.

Further, back in step, when the method reaches 420 from step 406, then the healthcare provider server device 104 transmits a first survey message to the user device 102(1) over the first communication channel and the method performs the steps 420-438 over the first communication channel instead of the second communication channel.

The disclosed embodiments provide an improved method of seamlessly switching between communication platforms. By seamlessly switching between communication platforms a care receiver 114(1) accesses on a second communication platform over a second communication channel previous messages communicated between the user device 102(1) and healthcare provider server device 104 on a first communication channel over a first communication platform. This results in an efficient communication method that provides care receiver 114(1) with access to vital information seamlessly over a plurality communication platforms and over multiple communication devices. Further, the disclosed embodiments provide technical advantages for care receiver 114(1) (e.g. patient) to access all their personal communications with a care provider 124(1) seamlessly over a single communication platform, thus reducing their efforts of logging into multiple communication platforms to access previous communications, resulting in an optimized user experience with minimal input from the care receiver 114(1).

The disclosed technology provides additionally security by providing an encrypted communication channel that terminates as and when required by the care receiver 114(1)-114(n) preference, the termination results it the messages communicated over the encrypted communication channel to be stored in a database rather than on the device itself. In some embodiments, the messages may be deleted after a predefined time period set by care receivers 114(1)-114(n), the predefined time period may include 1 day, 7 days, or 1 hour, although any other time period may be included. Further as the messages exchanged with care receivers 114(1)-114(n) are communicated over SMS messages or pre-installed web browser, care receivers 114(1)-114(n) do not require any additional mobile applications.

The web URL provided in step 408 expires after a predefined time period, this provides additional security to care receivers 114(1)-114(n) who share their user devices (1)-(n) with other users, the predefined time period may include 1 day, 7 days, or 1 hour, although any other time period may be included. In another example, the URL may expire after being clicked on a predefined number of times. Predefined number of times may include once, twice or five times, although any other number of times may also be included. While illustrative embodiments have been described herein, the scope thereof includes any and all embodiments having equivalent elements, modifications, omissions, combinations (e.g., of aspects across various embodiments), adaptations and/or alterations as would be appreciated by those in the art based on the present disclosure. For example, the number and orientation of components shown in the exemplary systems may be modified. Thus, the foregoing description has been presented for purposes of illustration only. It is not exhaustive and is not limiting to the precise forms or embodiments disclosed. Modifications and adaptations will be apparent to those skilled in the art from consideration of the specification and practice of the disclosed embodiments.

The elements in the claims are to be interpreted broadly based on the language employed in the claims and not limited to examples described in the present specification or during the prosecution of the application, which examples are to be construed as non-exclusive. It is intended, therefore, that the specification and examples be considered as exemplary only, with a true scope and spirit being indicated by the following claims and their full scope of equivalents.

The invention claimed is:

1. A computer implemented method for switching between communication platforms, the method being performed by a healthcare provider server device of a secure healthcare communication system, the method comprising:
   receiving a communication switch initiation request from a user device associated with a care receiver;
   transmitting an encoded message over a first communication channel to a first communication platform in response to receiving the communication switch initiation request, the encoded message including an identifier associated with a second communication platform;
   determining whether an encrypted communication initiation request is received;
   switching to a second communication channel from the first communication channel in response to receiving the encrypted communication initiation request, wherein the encrypted communication initiation request is generated based on the identifier;
   encrypting the second communication channel; and
   based on a determination that the encrypted communication request is not received, establishing a third communication channel and transmitting a communication switch request over the third communication channel to a third communication platform on the user device.

2. The method of claim 1, wherein one or more messages communicated over the first communication channel are stored in a database.

3. The method of claim 2, further comprising:
   retrieving the one or more messages communicated over the first communication channel from the database; and
   transmitting the retrieved one or more messages to the second communication platform over the second communication channel.

4. The method of claim 1, wherein the first communication channel and the second communication channel enable communication between the user device and the healthcare provider server.

5. The method of claim 1, wherein the user device is a smartphone, laptop or notebook computer, a tablet, a multifunctional watch, or a pair of multifunctional glasses.

6. The method of claim 1, wherein the identifier comprises at least one of a uniform resource locator (URL), a QR code, a barcode, or an embedded identifier.

7. The method of claim 1, wherein the first communication platform comprises a short messaging service (SMS) application, and the second communication platform comprises a web browser application, an audio calling application, or a video calling application.

8. The method of claim 1, further comprising:
   transmitting a first survey message to the second communication platform over the encrypted second communication channel after displaying a first set of messages; and
   receiving a response to the first survey message from the user device.

9. The method of claim 8, further comprising:
   determining whether the received response to the first survey message includes a numerical character;

identifying, when the received response to the first survey message includes the numerical character, a user response to the first survey message based on the numerical character; and updating a database with the identified user response.

10. The method of claim 8, further comprising:

determining whether the received response includes one or more non-numerical characters;

determining, when the received response includes the one or more non-numerical characters, whether the one or more non-numerical characters can be converted into a numerical character; and converting the one or more non-numerical characters into a numerical character based on the determination, wherein the numerical character is associated with a user response to the first survey message.

11. The method of claim 10, further comprising:

identifying the user response to the first survey message based on the numerical character; and updating a database with the identified user response to the first survey message.

12. A system for switching between communication platforms using a secure healthcare communication system, the system comprising:

one or more memory devices storing instructions; and one or more processors configured to execute the instructions to:

receive a communication switch initiation request from a user device associated with a care receiver;

transmit an encoded message over a first communication channel to a first communication platform in response to receiving the communication switch initiation request, the encoded message including an identifier associated with a second communication platform;

determine whether an encrypted communication initiation request is received, switch to a second communication channel from the first communication channel in response to receiving the encrypted communication initiation request, wherein the encrypted communication initiation request is generated based on the identifier;

encrypt the second communication channel; and based on a determination that the encrypted communication request is not received, establish a third communication channel and transmit a communication switch request over the third communication channel to a third communication platform on the user device.

13. The system of claim 12, wherein one or more messages communicated over the first communication channel are stored in a database.

14. The system of claim 13, the one or more processors being further configured to:

retrieve the one or more messages communicated over the first communication channel from the database; and transmit the retrieved one or more messages to the second communication platform over the second communication channel.

15. The system of claim 12, wherein the first communication channel and the second communication channel enable communication between the user device and a healthcare provider server.

16. The system of claim 12, the one or more processors being further configured to:

transmit a first survey message to the second communication platform over the encrypted second communication channel after displaying a first set of messages; and receive a response to the first survey message from the user device.

17. The system of claim 16, the one or more processors being further configured to:

determine whether the received response to the first survey message includes a numerical character;

identify, when the received response to the first survey message includes the numerical character, a user response to the first survey message based on the numerical character; and update a database with the identified user response.

18. The system of claim 16 the one or more processors being further configured to:

determine whether the received response includes one or more non-numerical characters;

determine, when the received response includes the one or more non-numerical characters, whether the one or more non-numerical characters can be converted into a numerical character; and convert the one or more non-numerical characters into a numerical character based on the determination, wherein the numerical character is associated with a user response to the first survey message.

19. The system of claim 18, the one or more processors being further configured to:

identify the user response to the first survey message based on the numerical character; and update a database with the identified user response to the first survey message.

* * * * *

UNITED STATES PATENT AND TRADEMARK OFFICE
CERTIFICATE OF CORRECTION

| | | |
|---|---|---|
| PATENT NO. | : 11,956,276 B2 | |
| APPLICATION NO. | : 17/934971 | |
| DATED | : April 9, 2024 | |
| INVENTOR(S) | : Howard Rosen et al. | |

It is certified that error appears in the above-identified patent and that said Letters Patent is hereby corrected as shown below:

On the Title Page

Item (57), in the Abstract, Line 2, "communication system the system" should read --communication system, the system--.

Item (57), in the Abstract, Lines 15-16, "Encrypted communication initiation request" should read --The encrypted communication initiation request--.

In the Claims

In Claim 18, Column 26, Line 31, "system of claim 16 the one or more" should read --system of claim 16, the one or more--.

Signed and Sealed this
Sixth Day of August, 2024

Katherine Kelly Vidal
*Director of the United States Patent and Trademark Office*